(12) United States Patent
Markosyan

(10) Patent No.: US 9,706,792 B2
(45) Date of Patent: *Jul. 18, 2017

(54) GLUCOSYL STEVIA COMPOSITION

(71) Applicant: PureCircle Sdn Bhd, Kuala Lumpur OT (MY)

(72) Inventor: Avetik Markosyan, Yerevan (AM)

(73) Assignee: PureCircle Sdn Bhd, Kuala Lumpur (MY)

( * ) Notice: Subject to any disclaimer, the term of this patent is extended or adjusted under 35 U.S.C. 154(b) by 20 days.

This patent is subject to a terminal disclaimer.

(21) Appl. No.: 14/616,010

(22) Filed: Feb. 6, 2015

(65) Prior Publication Data

US 2015/0164118 A1  Jun. 18, 2015

Related U.S. Application Data

(60) Continuation of application No. 14/073,423, filed on Nov. 6, 2013, now Pat. No. 8,993,269, which is a continuation of application No. 13/567,707, filed on Aug. 6, 2012, now Pat. No. 8,647,844, which is a division of application No. 13/029,263, filed on Feb. 17, 2011, now Pat. No. 8,257,948.

(51) Int. Cl.

| | | |
|---|---|---|
| *A23L 27/30* | (2016.01) | |
| *C12P 19/18* | (2006.01) | |
| *A23L 1/236* | (2006.01) | |
| *A23L 2/60* | (2006.01) | |
| *A61K 36/28* | (2006.01) | |
| *A21D 2/18* | (2006.01) | |
| *A21D 2/36* | (2006.01) | |
| *A23C 9/13* | (2006.01) | |
| *C12P 19/56* | (2006.01) | |
| *C12P 33/00* | (2006.01) | |
| *A61K 8/97* | (2017.01) | |
| *A61Q 11/00* | (2006.01) | |
| *A61K 8/60* | (2006.01) | |
| *A61Q 19/00* | (2006.01) | |

(52) U.S. Cl.
CPC .............. *A23L 1/2363* (2013.01); *A21D 2/18* (2013.01); *A21D 2/36* (2013.01); *A23C 9/1307* (2013.01); *A23L 2/60* (2013.01); *A23L 27/33* (2016.08); *A23L 27/36* (2016.08); *A61K 8/602* (2013.01); *A61K 8/97* (2013.01); *A61K 36/28* (2013.01); *A61Q 11/00* (2013.01); *A61Q 19/00* (2013.01); *C12P 19/18* (2013.01); *C12P 19/56* (2013.01); *C12P 33/00* (2013.01); *A23V 2002/00* (2013.01); *A61K 2800/10* (2013.01); *A61K 2800/805* (2013.01)

(58) Field of Classification Search
None
See application file for complete search history.

*Primary Examiner* — Robert Yamasaki
*Assistant Examiner* — Charles Zoltan Constantine
(74) *Attorney, Agent, or Firm* — Briggs and Morgan, P.A.; Audrey J. Babcock

(57) ABSTRACT

Glucosyl *stevia* compositions are prepared from steviol glycosides of *Stevia rebaudiana*Bertoni. The glucosylation was performed by cyclodextrin glucanotransferase using the starch as source of glucose residues. The short-chain glucosyl *stevia*compositions were purified to >95% content of total steviol glycosides. The compositions can be used as sweetness enhancers, flavor enhancers and sweeteners in foods, beverages, cosmetics and pharmaceuticals.

8 Claims, 3 Drawing Sheets

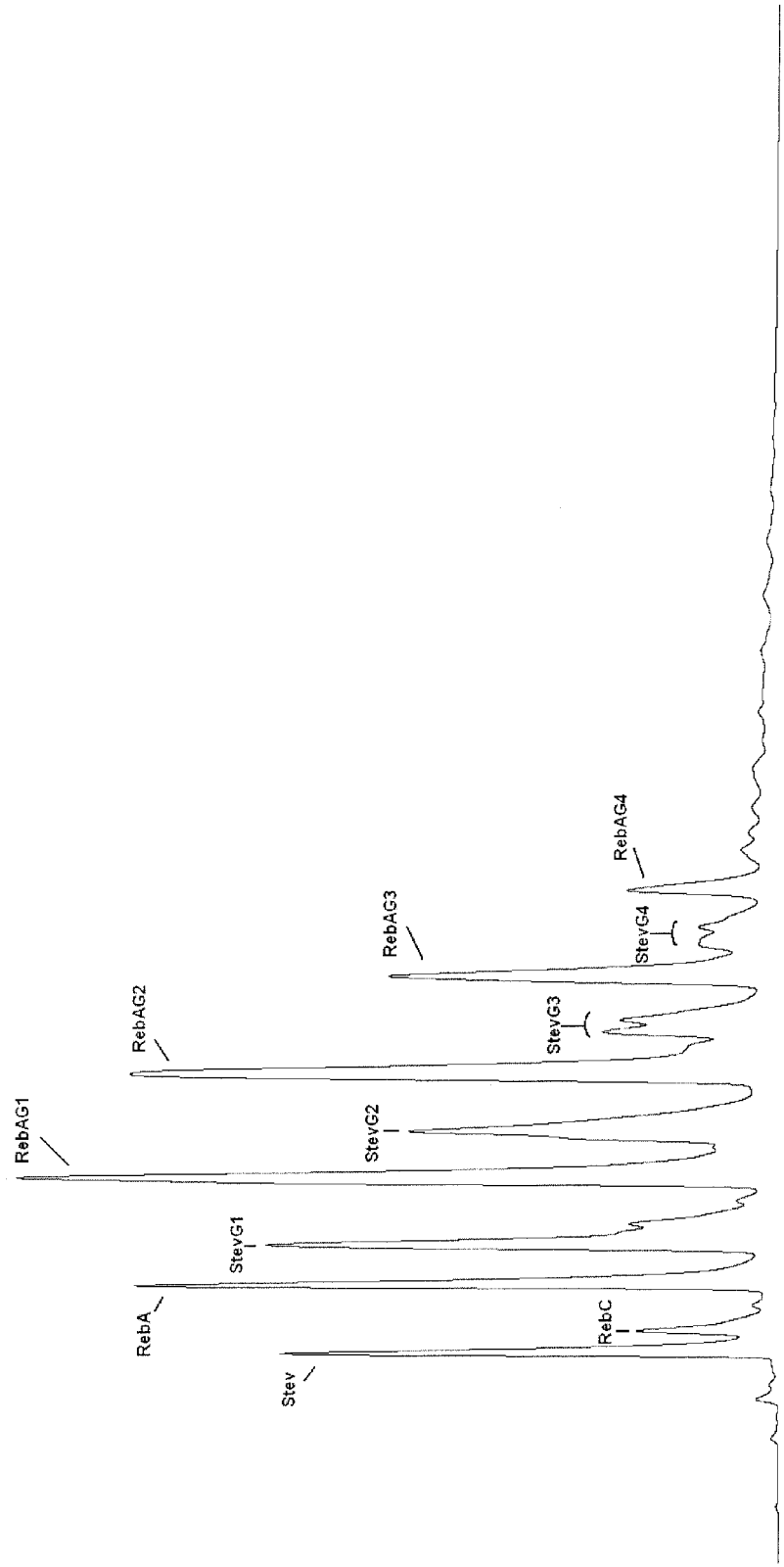

GLUCOSYL STEVIA COMPOSITION

CROSS REFERENCE TO RELATED APPLICATIONS

This application is a Continuation of U.S. patent application Ser. No. 14/073,423, filed Nov. 6, 2013, which is a Continuation of U.S. patent application Ser. No. 13/567,707, filed Aug. 6, 2012, now U.S. Pat. No. 8,647,844 issued Feb. 11, 2014, which is a Divisional of U.S. patent application Ser. No. 13/029,263, filed Feb. 17, 2011, now U.S. Pat. No. 8,257,948 issued Sep. 4, 2012, the contents of which applications are incorporated herein by reference in their entirety.

BACKGROUND OF THE INVENTION

Field of the Invention

The invention relates to a process for producing a highly purified food ingredient from the extract of the *Stevia rebaudiana* Bertoni plant and its use in various food products and beverages.

Description of the Related Art

Nowadays sugar alternatives are receiving increasing attention due to awareness of many diseases in conjunction with consumption of high-sugar foods and beverages. However many artificial sweeteners such as dulcin, sodium cyclamate and saccharin were banned or restricted in some countries due to concerns on their safety. Therefore non-caloric sweeteners of natural origin are becoming increasingly popular. The sweet herb *Stevia rebaudiana* Bertoni, produces a number of diterpene glycosides which feature high intensity sweetness and sensory properties superior to those of many other high potency sweeteners.

The above-mentioned sweet glycosides, have a common aglycon, steviol, and differ by the number and type of carbohydrate residues at the C13 and C19 positions. The leaves of *Stevia* are able to accumulate up to 10-20% (on dry weight basis) steviol glycosides. The major glycosides found in *Stevia* leaves are Rebaudioside A (2-10%), Stevioside (2-10%), and Rebaudioside C (1-2%). Other glycosides such as Rebaudioside B, D, E, and F, Steviolbioside and Rubusoside are found at much lower levels (approx. 0-0.2%).

Two major glycosides—Stevioside and Rebaudioside A, were extensively studied and characterized in terms of their suitability as commercial high intensity sweeteners. Stability studies in carbonated beverages confirmed their heat and pH stability (Chang S. S., Cook, J. M. (1983) Stability studies of stevioside and Rebaudioside A in carbonated beverages. *J. Agric. Food Chem.* 31: 409-412.)

Steviol glycosides differ from each other not only by molecular structure, but also by their taste properties. Usually stevioside is found to be 110-270 times sweeter than sucrose, Rebaudioside A between 150 and 320 times, and Rebaudioside C between 40-60 times sweeter than sucrose. Dulcoside A is 30 times sweeter than sucrose. Rebaudioside A has the least astringent, the least bitter, and the least persistent aftertaste thus possessing the most favorable sensory attributes in major steviol glycosides (Tanaka O. (1987) Improvement of taste of natural sweetners. *Pure Appl. Chem.* 69:675-683; Phillips K. C. (1989) *Stevia*: steps in developing a new sweetener. In: Grenby T. H. ed. Developments in sweeteners, vol. 3. Elsevier Applied Science, London. 1-43.)

Methods for the extraction and purification of sweet glycosides from the *Stevia rebaudiana* plant using water or organic solvents are described in, for example, U.S. Pat. Nos. 4,361,697; 4,082,858; 4,892,938; 5,972,120; 5,962,678; 7,838,044 and 7,862,845.

However, even in a highly purified state, steviol glycosides still possess undesirable taste attributes such as bitterness, sweet aftertaste, licorice flavor, etc. One of the main obstacles for the successful commercialization of *stevia* sweeteners are these undesirable taste attributes. It was shown that these flavor notes become more prominent as the concentration of steviol glycosides increases (Prakash I., DuBois G. E., Clos J. F., Wilkens K. L., Fosdick L. E. (2008) Development of rebiana, a natural, non-caloric sweetener. Food Chem. Toxicol., 46, S75-S82.)

On the other hand, replacing large amounts of sugar in the formulations brings up such problems as reduced mouthfeel, incomplete flavor profile etc. Therefore the application of high intensity low calorie sweeteners has to provide solutions to address these problems.

Thus, if a single composition will be able to deliver not only sweetness, but also possess flavor enhancing properties and correct the incomplete mouthfeel associated with the elimination of sucrose from food and beverage formulations, it will certainly be advantageous compared to other high intensity sweeteners known in the art.

Some of these undesirable properties can be reduced or eliminated by subjecting steviol glycosides to the reaction of intermolecular transglycosylation, when new carbohydrate residues are attached to initial molecule at C13 and C19 positions. Depending on the number of carbohydrate residues in these positions the quality and potency of the compounds taste will vary.

Pullulanase, isomaltase (Lobov S. V., Jasai R., Ohtani K., Tanaka O. Yamasaki K. (1991) Enzymatic production of sweet stevioside derivatives: transglycosylation by glucosidases. *Agric. Biol. Chem.* 55: 2959-2965), β-galactosidase (Kitahata S., Ishikawa S., Miyata T., Tanaka O. (1989) Production of rubusoside derivatives by transglycosylation of various β-galactosidase. *Agric. Biol. Chem.* 53: 2923-2928), and dextran saccharase (Yamamoto K., Yoshikawa K., Okada S. (1994) Effective production of glucosyl-stevioside by α-1,6-transglycosylation of dextran dextranase. *Biosci. Biotech. Biochem.* 58: 1657-1661) have been used as transglycosylating enzymes, together with pullulan, maltose, lactose, and partially hydrolyzed starch, respectively, as donors of glycosidic residues.

The transglycosylation of steviol glycosides was also performed by action of cyclodextrin glucanotransferases (CGTase) produced by *Bacillus stearothermophilus* (U.S. Pat. Nos. 4,219,571, and 7,807,206) as a result α-1,4-glucosyl derivatives were formed with degree of polymerization up to 10.

The treatment of transglucosylated stevioside with β-amylase resulted in a product consisting of mono- or di-α-1,4-glucosyl derivatives (Tanaka, 1987).

It was shown that the taste profile and sweetness power of glucosyl derivatives are largely dependent on number of additional glucosyl derivatives, i.e. the degree of polymerization of the α-1,4-glucosyl chain. The increase in number of α-1,4-glucosyl residues improved the taste quality but at the same time reduced the sweetness level (Tanaka, 1987).

It is noted also that many glucosyl *stevia* products contain up to 20% residual dextrins which do not possess significant functional properties and reduce the content of steviol glycosides in the product.

Therefore it is necessary to develop high purity products with optimal α-1,4-glucosyl chain length which will deliver the best combination of sweetness potency and flavor profile.

SUMMARY OF THE INVENTION

The present invention is aimed to overcome the disadvantages of existing *Stevia* sweeteners. The invention describes a process for producing a high purity food ingredient from the extract of the *Stevia rebaudiana* Bertoni plant and use thereof in various food products and beverages as a sweetness and flavor modifier.

The invention, in part, pertains to an ingredient comprising glucosylated derivatives of steviol glycosides of *Stevia rebaudiana* Bertoni plant. The steviol glycodsides are selected from the group consisting of stevioside, Rebaudioside A, Rebaudioside B, Rebaudioside C, Rebaudioside D, Rebaudioside E, Rebaudioside F, dulcoside A, steviolbioside, rubusoside, as well as other steviol glycosides found in *Stevia rebaudiana* Bertoni plant and mixtures thereof.

The invention, in part, pertains to a process for producing an ingredient containing glucosylated forms of stevioside, Rebaudioside A, Rebaudioside B, Rebaudioside C, Rebaudioside D, Rebaudioside E, Rebaudioside F, dulcoside A, steviolbioside, rubusoside, as well as other steviol glycosides found in *Stevia rebaudiana* Bertoni plant. The process can be an enzymatic transglucosylating process using CGTases produced by cultures of *Bacillus stearothermophilus*. The process may include the step of shortening glucosyl chains by β-amylase. The process can also have the steps of decolorizing, desalting and removing maltooligosaccharides. The decolorizing can be performed using activated carbon. The desalting can be performed by passing through ion exchange resins and/or membrane filters. Removing the maltooligosaccharides can be performed by passing through macroporuos polymeric resin.

In the invention, *Stevia* extract commercialized by PureCircle (JiangXi) Co., Ltd. (China), containing stevioside (28-30%), Rebaudioside A (50-55%), Rebaudioside C (9-12%), Rebaudioside F (1-3%) and other glycosides amounting to total steviol glycosides' content of at least 95%, was used as a starting material. Alternatively *stevia* extracts with different ratio of steviol glycosides as well as highly purified steviol glycosides such as Rebaudioside A, stevioside, Rebaudioside D, rubusoside etc, may be used as starting materials.

The starting material was subjected to the enzymatic transglucosylation by action of cyclodextrin glycosyltransferase (CGTase) in the presence of starch as a glucose donor. As a result α-1,4-glucosyl derivatives were formed with degree of polymerization up to 10. Then the formed derivatives were subjected to treatment with β-amylase to produce α-1,4-glucosyl derivatives possessing a specific degree of polymerization.

The oligosaccharides from obtained reaction mixture were removed by Amberlite XAD7 HP resin, and then decolorized, deionized, concentrated and spray dried.

The obtained products were applied in various foods and beverages as sweeteners, sweetener enhancers and flavor modifiers, including ice cream, cookies, bread, fruit juices, milk products, baked goods and confectionary products.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

FIG. 3 shows a high-performance liquid chromatographic chromatogram of purified transglucosylated *Stevia* extract after β-amylase treatment with short-chain (containing four or less α-1,4-glucosyl residues) derivatives of stevioside and Rebaudioside A.

DETAILED DESCRIPTION OF THE INVENTION

Figure 1:
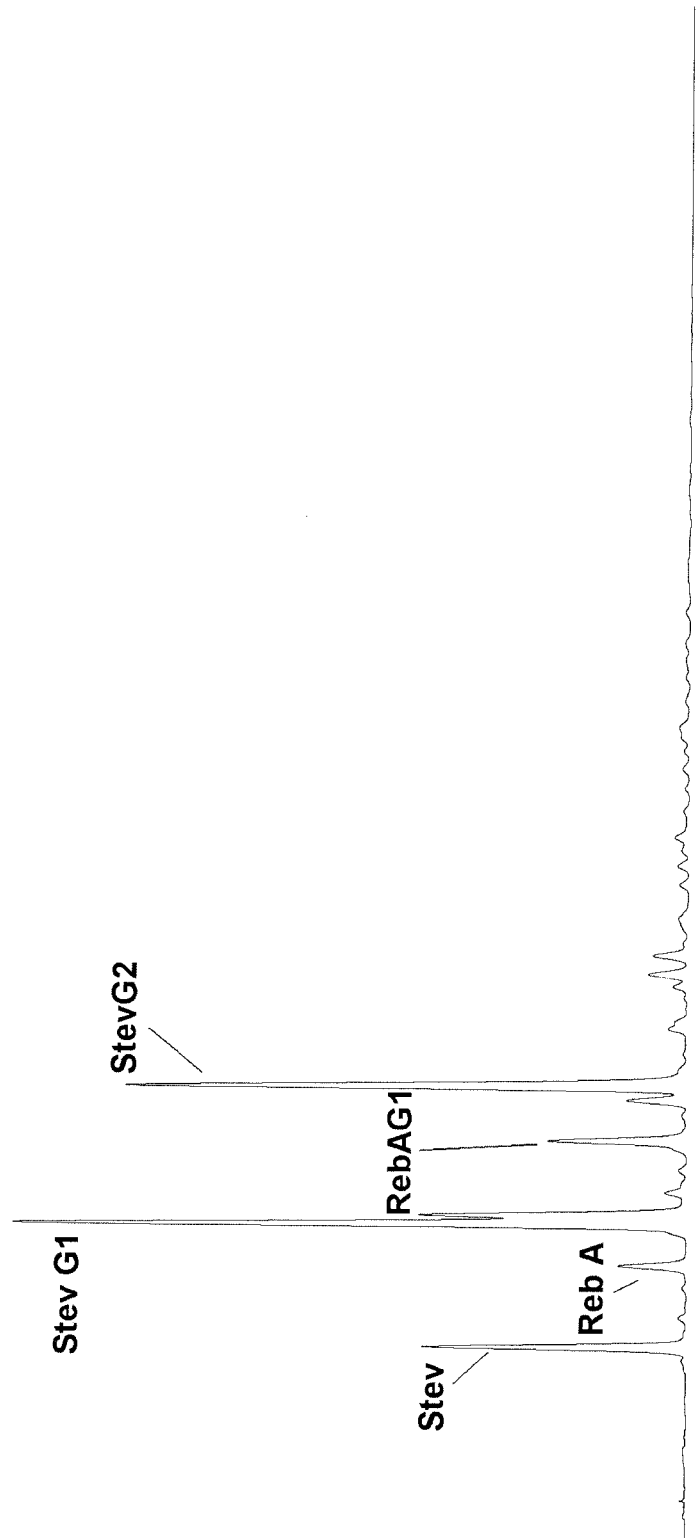
FIG. 1 shows a high-performance liquid chromatographic (HPLC) chart of commercial β-amylase treated product containing only mono- and di-α-1,4-glucosyl-derivatives of steviol glycosides.
Figure 2:
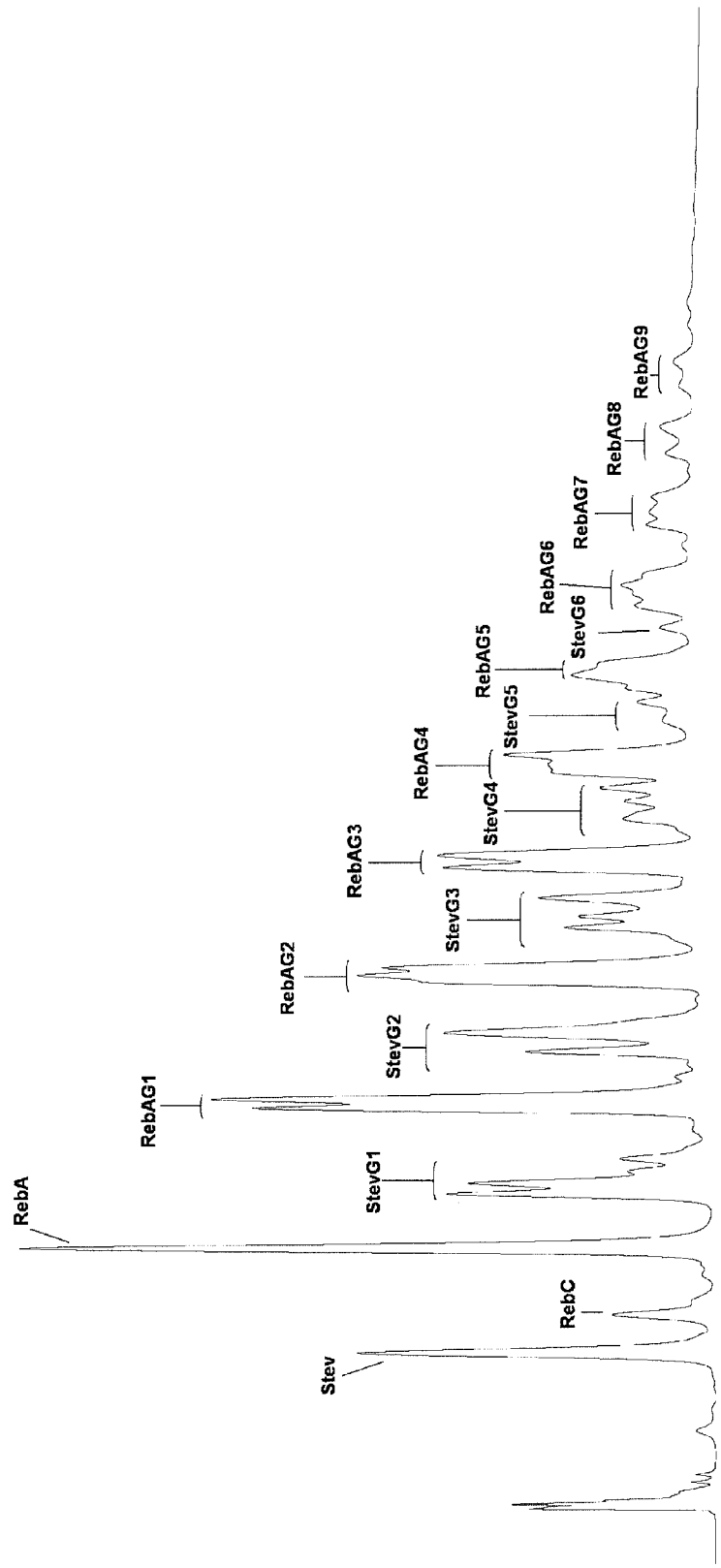
FIG. 2 shows a high-performance liquid chromatographic chromatogram of purified transglucosylated *Stevia* extract without β-amylase treatment containing long-chain α-1,4-glucosyl-derivatives with up to nine α-1,4-glucosyl residues.

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

*Stevia* extract commercialized by PureCircle (JiangXi) Co., Ltd. (China), containing stevioside (28-30%), Rebaudioside A (50-55%), Rebaudioside C (9-12%), Rebaudioside F (1-3%) and other glycosides (hereinafter collectively, "steviol glycosides") amounting to total steviol glycosides content of at least 95%, was used as a starting material. Alternatively *stevia* extracts with different ratio of steviol glycosides as well as highly purified steviol glycosides such as Rebaudioside A, stevioside, Rebaudioside D, rubusoside etc, may be used as starting materials.

The HPLC analysis of the raw materials and products was performed on Agilent Technologies 1200 Series (USA) liquid chromarograph, equipped with Zorbax-$NH_2$ (4.6×250 mm) column. The mobile phase was acetonitrile-water gradient from 80:20, v/v (0-2 min) to 50:50, v/v (2-70 min). A diode array detector set at 210 nm was used as the detector.

The transglucosylation was accomplished by cyclomaltodextrin glucanotransferases (CGTases; EC 2.4.1.19) produced by *Bacillus stearothermophilus* St-88 (PureCircle Sdn Bhd Collection of Industrial Microorganisms—Malaysia). However, any other CGTase or enzyme possessing intermolecular transglucosylation activity may be applied as well. The enzyme can be in a form of cell-free culture broth, concentrated liquid cell-free culture broth, spray dried or freeze dried cell-free culture broth, or high purity protein. Free and immobilized enzyme preparations can be used.

The activity of CGTase preparations was determined according to the procedure described in Hale W. S., Rawlins L. C. (1951) Amylase of *Bacillus macerans*. Cereal Chem. 28, 49-58.

Starches of different origin may be used as donors of glucosyl units such as, derived from wheat, corn, potato, tapioca, and sago.

Starch was subjected to partial hydrolysis (liquefaction) prior to the transglycosylation reaction. The dextrose equivalent of the partially hydrolyzed starch can be in the range of about 10-25, preferably about 12-16. Any enzyme capable of starch hydrolysis may be used for liquefaction, such as α-amylases, β-amylases etc. In one embodiment, CGTase and α-amylase mixtures as liquefying enzymes are preferred.

α-Amylase activity is expressed in Kilo Novo α-amylase Units (KNU). One KNU is the amount of α-amylase which, under standard conditions (pH 7.1; 37° C.), dextrinizes 5.26 g starch dry substance per hour.

The liquefaction mixture contains about 0.001-0.2 KNU, preferably about 0.05-0.1 KNU of α-amylase per one unit of CGTase.

The use of α-amylase in liquefaction allows achieving higher throughputs in further activated carbon filtration. When the CGTase is used as the only liquefying enzyme the filtration rate is approximately 10-15 L/hr per 1 $m^2$ of filter surface. In case of liquefaction enzyme mixture (comprising α-amylase and CGTase) the filtration rate is twice as fast—approximately 20-30 L/hr per 1 $m^2$ of filter surface.

The ratio of starch and CGTase in the liquefaction mixture is about 0.1-0.5 units per one gram of starch, preferably about 0.2-0.4 units per gram.

The concentration of starch in liquefaction mixture is about 15-40% (wt/wt), preferably about 20-30%.

The liquefaction is conducted at about 70-90° C. during about 0.5-5 hours, preferably about 1-2 hours.

After liquefaction, the reaction mixture is subjected to thermal inactivation of α-amylase at low pH conditions. The preferred pH range for inactivation is about pH 2.5 to pH 3.0 and preferred temperature is about 95-105° C. The duration of thermal inactivation is about 5-10 minutes.

After the inactivation, the pH of the reaction mixture is adjusted to about pH 5.5-6.5 and the steviol glycosides are added to the mixture and dissolved. The preferred ratio of steviol glycosides to starch (kg of steviol glycosides per 1 kg of starch) is about 0.5-1.5, preferably about 0.8-1.2.

A second portion of CGTase preparation is added and the transglucosylation reaction is conducted at about 65° C. for about 24-48 hours. The amount of the second portion of CGTase is about 0.2-4 units of CGTase per gram of solids, preferably about 0.5-1.2 units per gram of solids.

Upon completion of transglucosylation reaction, about 30-50 units per gram of solids of β-amylase was added and the reaction was continued for about 12-16 hours at about 35-55° C., preferably about 45° C. Soybean β-amylase was used in this stage. However β-amylases derived from any other source including barley, bacterial, fungal β-amylases and others may be used as well.

β-Amylase activity unit (1 AUN) is defined as the activity which liberates 100 μg of reducing sugar (expressed by dextrose equivalent) per minute under the following conditions: 1 mL of enzyme solution is mixed with 5 mL of 1.2% starch solution (pH 5.5, M/20 Acetate Buffer) and kept for 20 min at 40° C.

The reaction was stopped by heating at about 95° C. for about 15 minutes to inactivate the enzymes, and the solution was treated with activated carbon, to obtain decolorized reaction mixture. The amount of activated carbon was about 0.02-0.4 grams per gram of solids, preferably about 0.05-0.2 grams per gram of solids.

The decolorized reaction mixture was desalted by passing through ion exchange resins, such as Amberlite FPC23 ($H^+$ type) and Amberlite FPA51 ($OH^-$ type). Other appropriate decolorizing and desalting methods, such as membrane filtration, or other methods known in the art can be used.

The desalted reaction mixture was further concentrated by vacuum evaporator and dried by means of a spray dryer. Other appropriate concentrating and drying methods, such as membrane filtration, freeze drying, or other methods known to art can be used. The resulting product contains non-modified glycosides, short-chain (containing four or less α-1,4-glucosyl residues) derivatives and a mixture of maltooligosaccharides (Sample 1).

In order to prepare a product with higher content of total sweet glycosides (the sum of glycosylated and non-glycosylated glycosides), the maltooligosaccharides were removed using Amberlite XAD7 HP prior to the desalting treatment. The steviol glycosides and their glucosylated derivatives were adsorbed on the resin and subsequently eluted by aqueous ethanol. The resulted aqueous ethanol eluate, containing glucosyl steviol glycosides, was subsequently decolorized and desalted as described above and the glycosides solution, after the evaporation of eluting solvent, was powdered by spray drying. The resulting product contains non-modified glycosides, and short-chain (containing four or less α-1,4-glucosyl residues) derivatives (Sample 2).

The embodiments of the invention exemplified by Samples 1 and 2 are free or substantially free of higher glucosylated derivatives having more than 4 glucosyl residues. In accordance with this invention, the highly purified glucosyl *stevia* composition preferably comprises greater than about 25% by weight di-, tri- and tetraglucosyl Rebaudioside A, and greater than about 9% by weight tri- and tetraglucosyl steviosides.

Using a similar process as for sample 2, with exclusion of the β-amylase treatment stage, a product containing non-modified glycosides and long chain α-1,4-glucosyl-derivatives (with up to nine α-1,4-glucosyl residues) was prepared (Sample 3).

As a control, a commercial β-amylase treated product containing non-modified glycosides, and short-chain (containing two or less α-1,4-glucosyl residues) derivatives was used (Sample 4). The composition of the samples is summarized in Table 1.

TABLE 1

Composition of glucosyl steviol glycosides samples

| Compounds | Content, % | | | |
|---|---|---|---|---|
| | Sample 1 | Sample 2 | Sample 3 | Sample 4 |
| Stevioside | 2.5 | 3.0 | 3.1 | 9.5 |
| Rebaudioside C | 0.9 | 1.0 | 1.0 | 0.4 |
| Rebaudioside A | 5.2 | 6.1 | 6.0 | 2.8 |
| Monoglucosyl-stevioside (StevG1) | 11.0 | 13.2 | 7.4 | 34.9 |
| Monoglucosyl-Rebaudioside A (RebAG1) | 14.6 | 17.5 | 11.1 | 6.3 |
| Diglucosyl-stevioside (StevG2) | 10.4 | 12.4 | 8.4 | 26.4 |
| Diglucosyl-Rebaudioside A (RebAG2) | 15.6 | 18.6 | 9.6 | — |
| Triglucosyl-stevioside (StevG3) | 5.8 | 7.0 | 6.3 | — |

TABLE 1-continued

Composition of glucosyl steviol glycosides samples

| Compounds | Content, % | | | |
|---|---|---|---|---|
| | Sample 1 | Sample 2 | Sample 3 | Sample 4 |
| Triglucosyl-Rebaudioside A (RebAG3) | 7.9 | 9.5 | 7.7 | — |
| Tetraglucosyl-stevioside (StevG4) | 3.7 | 4.4 | 5.6 | — |
| Tetraglucosyl-Rebaudioside A (RebAG4) | 2.9 | 3.4 | 6.1 | — |
| Higher glucosylated derivatives | | | 22.7 | — |
| Total content of glycosides | 80.5 | 96.1 | 95.0 | 80.3 |

The sensory assessment of samples was carried using aqueous solutions, with 20 panelists. Based on overall acceptance the most desirable and most undesirable samples were chosen. The results are shown in Table 2.

TABLE 2

Sensory assessment of samples in water system

| Judgment | Sample 1 | Sample 2 | Sample 3 | Sample 4 |
|---|---|---|---|---|
| Most desirable | 5 | 11 | 1 | 2 |
| Most undesirable | 1 | 0 | 7 | 12 |
| Sweetness power | 150 | 160 | 120 | 150 |
| Comments | Sweet, light, soft, round, pleasant, almost similar to sucrose, no lingering aftertaste, sweetness onset is rapid | Sweet, light, soft, round, pleasant, similar to sucrose, no lingering aftertaste, sweetness onset is rapid | Sweet, slightly bitter, astringent, no lingering aftertaste, sweetness onset is moderate | Sweet, slightly bitter, astringent, slight lingering aftertaste, sweetness onset is slow |

As apparent from the results in Table 2, the sweetness quality of the Samples 1 and 2 was rated as most superior. Overall the samples with short-chain (containing four or less α-1,4-glucosyl residues) derivatives (No 1, and No. 2) possessed better taste profiles compared to samples with long-chain glucosyl derivatives (No. 3) and two or less α-1,4-glucosyl residues short-chain derivatives (No. 4).

Samples 1 and 2 show comparable sweetness power (150-160 times sweeter compared to a 5% sucrose solution) with control Sample 4 (150 times); however their flavor profile was clearly superior to the control sample.

The compositions can be used as sweetness enhancers, flavor enhancers and sweeteners in various food and beverage products. Non-limiting examples of food and beverage products include carbonated soft drinks, ready to drink beverages, energy drinks, isotonic drinks, low-calorie drinks, zero-calorie drinks, sports drinks, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, tabletop sweeteners, fruits and vegetables.

Additionally the compositions can be used in drug or pharmaceutical preparations and cosmetics, including but not limited to toothpaste, mouthwash, cough syrup, chewable tablets, lozenges, vitamin preparations, and the like.

The compositions can be used "as-is" or in combination with other sweeteners, flavors and food ingredients.

Non-limiting examples of sweeteners include steviol glycosides, stevioside, Rebaudioside A, Rebaudioside B, Rebaudioside C, Rebaudioside D, Rebaudioside E, Rebaudioside F, dulcoside A, steviolbioside, rubusoside, as well as other steviol glycosides found in *Stevia rebaudiana* Bertoni plant and mixtures thereof, stevia extract, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols.

Non-limiting examples of flavors include lemon, orange, fruity, banana, grape, pear, pineapple, bitter almond, cola, cinnamon, sugar, cotton candy, vanilla flavors.

Non-limiting examples of other food ingredients include flavors, acidulants, organic and amino acids, coloring agents, bulking agents, modified starches, gums, texturizers, preservatives, antioxidants, emulsifiers, stabilisers, thickeners, gelling agents.

The following examples illustrate various embodiments of the invention. It will be understood that the invention is not limited to the materials, proportions, conditions and procedures set forth in the examples, which are only illustrative.

Example 1

Preparation of CGTase

A strain of *Bacillus stearothermophilus* St-88 was inoculated in 2,000 liters of sterilized culture medium containing 1.0% starch, 0.25% corn extract, 0.5% $(NH_4)_2SO_4$, and 0.2% $CaCO_3$ (pH 7.0-7.5) at 56° C. for 24 hrs with continuous aeration (2,000 L/min) and agitation (150 rpm). The obtained culture broth was filtered using Kerasep 0.1 μm ceramic membrane (Novasep, France) to separate the cells. The cell-free permeate was further concentrated 2-fold on Persep 10 kDa ultrafilters (Orelis, France). The activity of the enzyme was determined according to Hale, Rawlins (1951). A crude enzyme preparation with activity of about 2 unit/mL was obtained.

Example 2

Preparation of Short-Chain Glucosyl *Stevia* Composition 100 g of tapioca starch was suspended in 300 mL of water (pH 6.5). 2 KNU of α-amylase (Termamyl Classic, Novozymes, Denmark) and 30 units of CGTase obtained according to EXAMPLE 1 were added, and the liquefaction of starch was carried out at 80° C. for about one hour to dextrose equivalent about 15. The pH of reaction mixture was adjusted to pH 2.8 by hydrochloric acid and the mixture was boiled at 100° C. during 5 minutes to inactivate the enzymes. After cooling to 65° C., the pH was adjusted to pH 6.0 with sodium hydroxide solution. 100 g *stevia* extract produced by PureCircle (JiangXi) Co., Ltd. (China), containing stevioside 29.2%, Rebaudioside A 54.3%, Rebaudioside C 9.0%, Rebaudioside F (1.7%) and other glycosides amounting to total steviol glycosides content of about 96.4% was added to liquefied starch and stirred until a homogeneous solution was obtained. 200 units of CGTase was added to the solution and the mixture was held at a temperature of 65° C. for 24 hours under continuous agitation. Then the temperature was reduced to 45° C., and 8,000 units soybean β-amylase (#1500S, Nagase Chemtex Corp., Japan) was added to reaction mixture. The reaction was continued for another 12 hours. The obtained reaction mixture was heated at 95° C. for 15 minutes to inactivate the enzymes. 20 grams of activated carbon was added and the mixture was heated to 75° C. and held for 30 minutes. The mixture was filtered and the filtrate was diluted with water to 5% solids content and passed through columns packed with Amberlite FPC23 (H$^+$) and Amberlite FPA51 (OH$^-$) ion exchange resins. The desalted solution was concentrated at 60° C. under vacuum, and dried into a powder form using laboratory spray dryer. 196 grams of product was obtained (Sample 1).

Example 3

Preparation of Highly Purified Short-Chain Glucosyl *Stevia* Composition 100 g of tapioca starch was suspended in 300 mL of water (pH 6.5). 2 KNU of α-amylase (Termamyl Classic, Novozymes, Denmark) and 30 units of CGTase obtained according to EXAMPLE 1 were added, and the liquefaction of starch was carried out at 80° C. for about one hour to dextrose equivalent about 15. The pH of reaction mixture was adjusted to pH 2.8 by hydrochloric acid and the mixture was boiled at 100° C. during 5 minutes to inactivate the enzymes. After cooling to 65° C., the pH was adjusted to pH 6.0 with sodium hydroxide solution. 100 g *stevia* extract produced by PureCircle (JiangXi) Co., Ltd. (China), containing stevioside 29.2%, Rebaudioside A 54.3%, Rebaudioside C 9.0%, Rebaudioside F (1.7%) and other glycosides amounting to total steviol glycosides content of about 96.4% was added to liquefied starch and stirred until a homogeneous solution was obtained. 200 units of CGTase was added to the solution and the mixture was held at a temperature of 65° C. for 24 hours under continuous agitation. Then the temperature was reduced to 45° C., and 8,000 units soybean β-amylase (#1500S, Nagase Chemtex Corp., Japan) was added to reaction mixture. The reaction was continued for another 12 hours. The obtained reaction mixture was heated at 95° C. for 15 minutes to inactivate the enzymes. 20 grams of activated carbon was added and the mixture was heated to 75° C. and held for 30 minutes. The mixture was filtered and the filtrate was diluted with water to 5% solids content and passed through columns each packed with 4000 mL Amberlite XAD 7HP macroporous adsorbent resin. The columns were washed with 5 volumes of water and 2 volumes of 20% (v/v) ethanol. The adsorbed glycosides were eluted with 50% ethanol. Obtained eluate was passed through columns packed with Amberlite FPC23 (H$^+$) and Amberlite FPA51 (OH$^-$) ion exchange resins. The ethanol was evaporated and the desalted and decolorized water solution was concentrated at 60° C. under vacuum, then dried into a powder form using laboratory spray dryer. 151 grams of product was obtained (Sample 2).

Example 4

Preparation of Highly Purified Long-Chain Glucosyl *Stevia* Composition 100 g of tapioca starch was suspended in 300 mL of water (pH 6.5). 2 KNU of α-amylase (Termamyl Classic, Novozymes, Denmark) and 30 units of CGTase obtained according to EXAMPLE 1 were added, and the liquefaction of starch was carried out at 80° C. for about one hour to dextrose equivalent about 15. The pH of reaction mixture was adjusted to pH 2.8 by hydrochloric acid and the mixture was boiled at 100° C. during 5 minutes to inactivate the enzymes. After cooling to 65° C., the pH was adjusted to pH 6.0 with sodium hydroxide solution. 100 g *stevia* extract produced by PureCircle (JiangXi) Co., Ltd. (China), containing stevioside 29.2%, Rebaudioside A 54.3%, Rebaudioside C 9.0%, Rebaudioside F (1.7%) and other glycosides amounting to total steviol glycosides content of about 96.4% was added to liquefied starch and stirred until a homogeneous solution was obtained. 200 units of CGTase was added to the solution and the mixture was held at a temperature of 65° C. for 24 hours under continuous agitation. The obtained reaction mixture was heated at 95° C. for 15 minutes to inactivate the enzyme. 20 grams of activated carbon was added and the mixture was heated to 75° C. and held during 30 min. The mixture was filtered and the filtrate was diluted with water to 5% solids content and passed through columns each packed with 4000 mL Amberlite XAD 7HP macroporous adsorbent resin. The columns were washed with 5 volumes of water and 2 volumes of 20% (v/v) ethanol. The adsorbed glycosides were eluted with 50% ethanol. Obtained eluate was passed through columns packed with Amberlite FPC23 (H$^+$) and Amberlite FPA51 (OH$^-$) ion exchange resins. The ethanol was evaporated and the desalted and decolorized water solution was concentrated at 60° C. under vacuum, then dried into a powder form using laboratory spray dryer. 166 grams of product was obtained (Sample 3).

Example 5

Low-Calorie Orange Juice Drink

Orange concentrate (35%), citric acid (0.35%), ascorbic acid (0.05%), orange red color (0.01%), orange flavor (0.20%), Rebaudioside A (0.003%) and different glucosyl *stevia* compositions (0.03%) were blended and dissolved completely in water (up to 100%) and pasteurized. Glucosyl *stevia* compositions were represented by Samples 1, 2, and 3, obtained according to EXAMPLES 2, 3, and 4, respectively; and Sample 4 was a commercial β-amylase treated product (containing only mono- and di-α-1,4-glucosyl-derivatives of steviol glycosides).

The sensory evaluations of the samples are summarized in Table 3. The data show that the best results can be obtained by using the high purity short-chain glucosyl *stevia* compositions (containing four or less α-1,4-glucosyl residues) derivatives (Samples 1 and 2). Particularly the drinks prepared with Samples 1 and 2 exhibited a rounded and complete flavor profile and mouthfeel.

TABLE 3

Evaluation of orange juice drink samples

| Sample | Comments | | |
|---|---|---|---|
| | Flavor | Aftertaste | Mouthfeel |
| No. 1 | High quality sweetness, pleasant taste similar to sucrose, rounded and balanced flavor | Clean, almost no bitterness, no aftertaste | Full |
| No. 2 | High quality sweetness, pleasant taste similar to sucrose, rounded and balanced flavor | Clean, no bitterness and no aftertaste | Full |
| No. 3 | High quality sweetness, pleasant taste almost similar to sucrose, rounded and balanced flavor | Clean, almost no bitterness, no aftertaste | Almost acceptable |
| No. 4 | Sweet, licorice notes | Slight bitterness and aftertaste | Not acceptable |

The same method can be used to prepare juices and juice drinks from other fruits, such as apples, lemons, apricots, cherries, pineapples, mangoes, etc.

Example 6

Low-Calorie Carbonated Beverage

A carbonated beverage according to formula presented below was prepared.

| Ingredients | Quantity, % |
|---|---|
| Sucrose | 5.5 |
| Cola flavor | 0.340 |
| ortho-Phosphoric acid | 0.100 |
| Sodium citrate | 0.310 |
| Sodium benzoate | 0.018 |
| Citric acid | 0.018 |
| Rebaudioside A | 0.003 |
| Glucosyl stevia composition | 0.05 |
| Carbonated water | to 100 |

The sensory properties were evaluated by 20 panelists. The results are summarized in Table 4.

TABLE 4

Evaluation of low-calorie carbonated beverage samples

| | Number of panelists detected the attribute | | | |
|---|---|---|---|---|
| Taste attribute | Sample No. 1 | Sample No. 2 | Sample No. 3 | Sample No. 4 |
| Bitter taste | 0 | 0 | 2 | 20 |
| Astringent taste | 1 | 0 | 3 | 20 |
| Aftertaste | 1 | 0 | 2 | 20 |
| Comments | | | | |
| Quality of sweet taste | Clean (19 of 20) | Clean (20 of 20) | Clean (17 of 20) | Bitter aftertaste (5 of 20) |
| Overall evaluation | Satisfactory (18 of 20) | Satisfactory (20 of 20) | Satisfactory (15 of 20) | Satisfactory (3 of 20) |

The above results show that the beverages prepared using Samples 1 and 2 possessed the best organoleptic characteristics.

Example 7

Diet Cookies

Flour (50.0%), margarine (30.0%) fructose (10.0%), maltitol (8.0%), whole milk (1.0%), salt (0.2%), baking powder (0.15%), vanillin (0.1%) and different glucosyl *stevia* compositions (0.03%) were kneaded well in dough-mixing machine. The obtained dough was molded and baked in oven at 200° C. for 15 minutes. Glucosyl *stevia* compositions were by represented by Samples 1, 2, and 3, obtained according to EXAMPLES 2, 3, and 4, respectively; with Sample 4 being a commercial β-amylase treated product (containing only mono- and di-α-1,4-glucosyl-derivatives of steviol glycosides).

The sensory properties were evaluated by 20 panelists. The best results were obtained in samples prepared by high purity short-chain glucosyl *stevia* compositions (containing four or less α-1,4-glucosyl residues) derivatives (Samples 1 and 2). The panelists noted rounded and complete flavor profile and mouthfeel in cookies prepared with Samples 1 and 2.

Example 8

Yoghurt

Different glucosyl *stevia* compositions (0.03%) and sucrose (4%) were dissolved in low fat milk. Glucosyl *stevia* compositions were by represented by Samples 1, 2, and 3, obtained according to EXAMPLES 2, 3, and 4, respectively; with Sample 4 being a commercial β-amylase treated product (containing only mono- and di-α-1,4-glucosyl-derivatives of steviol glycosides). After pasteurizing at 82° C. for 20 minutes, the milk was cooled to 37° C. A starter culture (3%) was added and the mixture was incubated at 37° C. for 6 hours then at 5° C. for 12 hours.

The sensory properties were evaluated by 20 panelists. The best results were obtained in samples prepared by high purity short-chain glucosyl *stevia* compositions (containing four or less α-1,4-glucosyl residues) derivatives (Samples 1 and 2). The panelists noted rounded and complete flavor profile and mouthfeel in samples prepared with Samples 1 and 2.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

I claim:

1. A sweetener composition comprising a glucosyl *stevia* composition made by a process comprising the steps of:
   adding starch into water to form a starch suspension;
   adding a first hydrolyzing enzyme comprising a mixture of α-amylase and CGTase into the starch suspension and incubating for about 0.5 to 5 hours at about 70-90° C., resulting in a liquefied starch suspension;
   inactivating the α-amylase by low pH heat treatment;
   adding steviol glycosides into the liquefied starch suspension, resulting in a reaction mixture;
   adding a transglucosylation enzyme into the reaction mixture and incubating for about 24-48 hours at about 65° C. to transglucosylate the steviol glycosides, resulting in a glucosyl *stevia* composition; and
   adding an additional sweetening agent;
   wherein the glucosyl *stevia* composition comprises unmodified steviol glycosides and greater than about 34% by weight di-, tri- and tetraglucosyl steviol glycosides; and the additional sweetening agent is selected from the group consisting of: *stevia* extract, steviol glycosides, stevioside, Rebaudioside A, Rebaudioside B, Rebaudioside C, Rebaudioside D, Rebaudioside E, Rebaudioside F, dulcoside A, steviolbioside, rubusoside, other steviol glycosides found in *Stevia rebaudiana* Bertoni plant and mixtures thereof, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols, and a combination thereof.

2. The sweetener composition of claim 1, wherein the glucosyl *stevia* composition comprises greater than about 25% by weight di-, tri- and tetraglucosyl Rebaudioside A and greater than about 9% tri- and tetraglucosyl steviosides.

3. A flavor composition comprising a glucosyl *stevia* composition made by a process comprising the steps of:
   adding starch into water to form a starch suspension;
   adding a first hydrolyzing enzyme comprising a mixture of α-amylase and CGTase into the starch suspension and incubating for about 0.5 to 5 hours at about 70-90° C., resulting in a liquefied starch suspension;
   inactivating the α-amylase by low pH heat treatment;
   adding steviol glycosides into the liquefied starch suspension, resulting in a reaction mixture;
   adding a transglucosylation enzyme into the reaction mixture and incubating for about 24-48 hours at about 65° C. to transglucosylate the steviol glycosides, resulting in a glucosyl *stevia* composition; and
   adding an additional flavoring agent;
   wherein the glucosyl *stevia* composition comprises unmodified steviol glycosides and greater than about 34% by weight di-, tri- and tetraglucosyl steviol glycosidesid; and the additional flavoring agent is selected from the group consisting of: lemon, orange, fruity, banana, grape, pear, pineapple, mango, bitter almond, cola, cinnamon, sugar, cotton candy, vanilla, and a combination thereof.

4. The flavor composition of claim 3, wherein the glucosyl *stevia* composition comprises greater than about 25% by weight di-, tri- and tetraglucosyl Rebaudioside A and greater than about 9% tri- and tetraglucosyl steviosides.

5. A food ingredient comprising a glucosyl *stevia* composition made by a process comprising the steps of:
   adding starch into water to form a starch suspension;
   adding a first hydrolyzing enzyme comprising a mixture of α-amylase and CGTase into the starch suspension and incubating for about 0.5 to 5 hours at about 70-90° C., resulting in a liquefied starch suspension;
   inactivating the α-amylase by low pH heat treatment;
   adding steviol glycosides into the liquefied starch suspension, resulting in a reaction mixture;
   adding a transglucosylation enzyme into the reaction mixture and incubating for about 24-48 hours at about 65° C. to transglucosylate the steviol glycosides, resulting in a glucosyl *stevia* composition; and
   adding an additional food ingredient;
   wherein the glucosyl *stevia* composition comprises unmodified steviol glycosides and greater than about 34% by weight di-, tri- and tetraglucosyl steviol glycosides; and the additional food ingredient is selected from the group consisting of: acidulants, organic and amino acids, coloring agents, bulking agents, modified starches, gums, texturizers, preservatives, antioxidants, emulsifiers, stabilisers, thickeners, gelling agents, and a combination thereof.

6. The food ingredient of claim 5, wherein the glucosyl *stevia* composition comprises greater than about 25% by weight di-, tri- and tetraglucosyl Rebaudioside A and greater than about 9% tri- and tetraglucosyl steviosides.

7. A food, beverage, cosmetic or pharmaceutical product comprising a glucosyl *stevia* composition made by a process comprising the steps of:
   adding starch into water to form a starch suspension;
   adding a first hydrolyzing enzyme comprising a mixture of α-amylase and CGTase into the starch suspension and incubating for about 0.5 to 5 hours at about 70 -90 ° C., resulting in a liquefied starch suspension;
   inactivating the α-amylase by low pH heat treatment;
   adding steviol glycosides into the liquefied starch suspension, resulting in a reaction mixture; and
   adding a transglucosylation enzyme into the reaction mixture and incubating for about 24-48 hours at about 65° C. to transglucosylate the steviol glycosides, resulting in a glucosyl *stevia* composition;
   wherein the glucosyl *stevia* composition comprises unmodified steviol glycosides and greater than about 34% by weight di-, tri- and tetraglucosyl steviol glycosides.

8. The food, beverage, cosmetic or pharmaceutical product of claim 7, wherein the glucosyl *stevia* composition comprises greater than about 25% by weight di-, tri-and tetraglucosyl Rebaudioside A and greater than about 9% tri- and tetraglucosyl steviosides.

* * * * *